(12) United States Patent
Sinofsky et al.

(10) Patent No.: US 8,900,219 B2
(45) Date of Patent: Dec. 2, 2014

(54) SYSTEM AND METHOD FOR VISUALIZING TISSUE DURING ABLATION PROCEDURES

(75) Inventors: Edward L. Sinofsky, Dennis, MA (US); Gerald Melsky, Lexington, MA (US); Stephen W. Sagon, Amherst, NH (US); Norman E. Farr, Woods Hole, MA (US)

(73) Assignee: Cardiofocus, Inc., Marlborough, MA (US)

( * ) Notice: Subject to any disclaimer, the term of this patent is extended or adjusted under 35 U.S.C. 154(b) by 1378 days.

(21) Appl. No.: 12/423,137

(22) Filed: Apr. 14, 2009

(65) Prior Publication Data

US 2009/0326320 A1    Dec. 31, 2009

Related U.S. Application Data

(63) Continuation-in-part of application No. 10/865,558, filed on Jun. 10, 2004, now Pat. No. 8,540,704, which
(Continued)

(51) Int. Cl.
| | |
|---|---|
| *A61B 18/20* | (2006.01) |
| *A61B 5/00* | (2006.01) |
| *A61B 1/06* | (2006.01) |
| *A61B 18/24* | (2006.01) |
| *A61B 18/00* | (2006.01) |
| *A61B 1/00* | (2006.01) |
| *A61B 17/00* | (2006.01) |

(52) U.S. Cl.
CPC ....... *A61B 18/24* (2013.01); *A61B 2018/00011* (2013.01); *A61B 1/00165* (2013.01); *A61B 5/0084* (2013.01); *A61B 5/0075* (2013.01); *A61B 1/0638* (2013.01); *A61B 2017/00057* (2013.01)
USPC .................................................. 606/2; 606/3

(58) Field of Classification Search
USPC ...................... 606/2, 14–16, 32, 41
See application file for complete search history.

(56) References Cited

U.S. PATENT DOCUMENTS

| | | | |
|---|---|---|---|
| 3,417,745 | A | 12/1968 | Sheldon |
| 3,821,510 | A | 6/1974 | Muncheryan |
(Continued)

FOREIGN PATENT DOCUMENTS

| | | |
|---|---|---|
| DE | 94117543 | 11/1994 |
| EP | 0214712 | 3/1987 |
(Continued)

OTHER PUBLICATIONS

Bredikis, J. et al. "Laser Destruction of the Atrioventricular Bundle Using the Cardiac Endoscope" Kardiologiia, 1988, 28(8): 94-96.
(Continued)

*Primary Examiner* — Aaron Roane
(74) *Attorney, Agent, or Firm* — Leason Ellis LLP

(57) ABSTRACT

Systems for visualizing cardiac tissue during an ablation procedure are provided. In general, the systems include an imaging module configured to measure absorbance data at first and second wavelengths wherein the ratio of these absorbance values identifies the nature of the tissue (e.g., lesion, de novo tissue, etc.). The imaging module can also include a video system having at least two chips with corresponding bandpass filters centered at the first and second target wavelengths. The system can also include a processor and/or video monitor for combining the images produced by the various chips, determining treated and non-treated tissue based on the ratio of absorbance values at the target wavelengths, and displaying images of the treatment area. Methods of visualizing cardiac treatment areas during ablation procedures are also provided herein.

13 Claims, 10 Drawing Sheets

Related U.S. Application Data is a continuation-in-part of application No. 09/924,393, filed on Aug. 7, 2001, now Pat. No. 6,676,656, which is a continuation-in-part of application No. 10/357,156, filed on Feb. 3, 2003, now Pat. No. 8,025,661, said application No. 10/865,558 is a continuation-in-part of application No. 10/674,114, filed on Sep. 29, 2003, now Pat. No. 6,942,657, which is a continuation of application No. 09/616,275, filed on Jul. 14, 2000, now Pat. No. 6,626,900, which is a continuation-in-part of application No. 09/602,420, filed on Jun. 23, 2000, now Pat. No. 6,572,609, which is a continuation-in-part of application No. 09/357,355, filed on Jul. 14, 1999, now Pat. No. 6,423,055.

(60) Provisional application No. 60/477,374, filed on Jun. 10, 2003.

(56) References Cited

U.S. PATENT DOCUMENTS

| | | | |
|---|---|---|---|
| 4,224,929 A | 9/1980 | Furihata | |
| 4,233,493 A | 11/1980 | Nath et al. | |
| 4,273,109 A | 6/1981 | Enderby | |
| 4,336,809 A | 6/1982 | Clark | |
| 4,445,892 A | 5/1984 | Hussein et al. | |
| 4,585,298 A | 4/1986 | Mori et al. | |
| 4,625,724 A | 12/1986 | Suzuki et al. | |
| 4,660,925 A | 4/1987 | McCaughan, Jr. | |
| 4,701,166 A | 10/1987 | Groshong et al. | |
| 4,718,417 A | 1/1988 | Kittrell et al. | |
| 4,770,653 A | 9/1988 | Shturman | |
| 4,781,681 A | 11/1988 | Sharrow et al. | |
| 4,819,632 A | 4/1989 | Davies et al. | |
| 4,842,390 A | 6/1989 | Sottini et al. | |
| 4,852,567 A | 8/1989 | Sinofsky | |
| 4,860,743 A | 8/1989 | Abela | |
| 4,862,886 A | 9/1989 | Clarke et al. | |
| 4,878,492 A | 11/1989 | Sinofsky et al. | |
| 4,878,725 A | 11/1989 | Hessel et al. | |
| 4,913,142 A | 4/1990 | Kittrell et al. | |
| 4,961,738 A | 10/1990 | Mackin | |
| 5,026,367 A | 6/1991 | Leckrone et al. | |
| 5,030,201 A | 7/1991 | Palestrant | |
| 5,053,033 A | 10/1991 | Clarke | |
| 5,071,417 A | 12/1991 | Sinofsky | |
| 5,078,681 A | 1/1992 | Kawashima et al. | |
| 5,090,959 A | 2/1992 | Samson et al. | |
| 5,109,859 A | 5/1992 | Jenkins | |
| 5,125,925 A | 6/1992 | Lundahl | |
| 5,133,709 A | 7/1992 | Prince | |
| 5,140,987 A | 8/1992 | Schuger et al. | |
| 5,151,096 A | 9/1992 | Khoury | |
| 5,151,097 A | 9/1992 | Daikuzono | |
| 5,163,935 A | 11/1992 | Black et al. | |
| 5,169,395 A | 12/1992 | Narciso, Jr. | |
| 5,188,632 A | 2/1993 | Goldenberg | |
| 5,188,634 A | 2/1993 | Hussein et al. | |
| 5,190,538 A | 3/1993 | Hussein et al. | |
| 5,196,005 A | 3/1993 | Doiron et al. | |
| 5,207,699 A | 5/1993 | Coe | |
| 5,209,748 A | 5/1993 | Daikuzono | |
| 5,219,346 A | 6/1993 | Wagnieres et al. | |
| 5,242,438 A | 9/1993 | Saadatmanesh et al. | |
| 5,261,904 A | 11/1993 | Baker et al. | |
| 5,269,777 A | 12/1993 | Doiron et al. | |
| RE34,544 E | 2/1994 | Spears | |
| 5,318,024 A | 6/1994 | Kittrell et al. | |
| 5,330,465 A | 7/1994 | Doiron et al. | |
| 5,337,381 A | 8/1994 | Biswas et al. | |
| 5,350,375 A | 9/1994 | Deckelbaum et al. | |
| 5,363,458 A | 11/1994 | Pan et al. | |
| 5,368,564 A | 11/1994 | Savage | |
| 5,374,953 A * | 12/1994 | Sasaki et al. | 348/65 |
| 5,380,316 A | 1/1995 | Aita et al. | |
| 5,380,317 A | 1/1995 | Everett et al. | |
| 5,395,362 A | 3/1995 | Sacharoff et al. | |
| 5,401,270 A | 3/1995 | Muller et al. | |
| 5,409,483 A * | 4/1995 | Campbell et al. | 606/15 |
| 5,417,653 A | 5/1995 | Sahota et al. | |
| 5,418,649 A | 5/1995 | Igarashi et al. | |
| 5,423,805 A | 6/1995 | Brucker et al. | |
| 5,427,119 A | 6/1995 | Swartz et al. | |
| 5,431,647 A | 7/1995 | Purcell, Jr. et al. | |
| 5,437,660 A | 8/1995 | Johnson et al. | |
| 5,441,497 A | 8/1995 | Narciso, Jr. | |
| 5,445,608 A | 8/1995 | Chen et al. | |
| 5,464,404 A | 11/1995 | Abela et al. | |
| 5,482,037 A | 1/1996 | Borghi | |
| 5,496,305 A | 3/1996 | Kittrell et al. | |
| 5,497,774 A | 3/1996 | Swartz et al. | |
| 5,507,725 A | 4/1996 | Savage et al. | |
| 5,531,664 A | 7/1996 | Adachi et al. | |
| 5,536,265 A | 7/1996 | van den Bergh et al. | |
| 5,575,766 A | 11/1996 | Swartz et al. | |
| 5,605,162 A | 2/1997 | Mirzaee et al. | |
| 5,613,965 A | 3/1997 | Muller | |
| 5,643,253 A | 7/1997 | Baxter et al. | |
| 5,649,923 A | 7/1997 | Gregory et al. | |
| 5,662,712 A | 9/1997 | Pathak et al. | |
| 5,680,860 A | 10/1997 | Imran | |
| 5,690,611 A | 11/1997 | Swartz et al. | |
| 5,693,043 A | 12/1997 | Kittrell et al. | |
| 5,700,243 A | 12/1997 | Narciso, Jr. | |
| 5,702,438 A | 12/1997 | Avitall | |
| 5,722,401 A | 3/1998 | Pietroski et al. | |
| 5,725,522 A | 3/1998 | Sinofsky | |
| 5,759,619 A | 6/1998 | Jin et al. | |
| 5,769,843 A | 6/1998 | Abela et al. | |
| 5,772,590 A | 6/1998 | Webster, Jr. | |
| 5,773,835 A | 6/1998 | Sinofsky | |
| 5,779,646 A | 7/1998 | Koblish et al. | |
| 5,782,239 A | 7/1998 | Webster, Jr. | |
| 5,782,899 A | 7/1998 | Imran | |
| 5,800,482 A | 9/1998 | Pomeranz et al. | |
| 5,807,395 A | 9/1998 | Mulier et al. | |
| 5,823,955 A | 10/1998 | Kuck et al. | |
| 5,824,005 A | 10/1998 | Motamedi et al. | |
| 5,830,209 A | 11/1998 | Savage et al. | |
| 5,833,682 A | 11/1998 | Amplatz et al. | |
| 5,843,073 A | 12/1998 | Sinofsky | |
| 5,845,646 A | 12/1998 | Lemelson | |
| 5,860,974 A | 1/1999 | Abele | |
| 5,885,278 A | 3/1999 | Fleischman | |
| 5,891,133 A | 4/1999 | Murphy-Chutorian | |
| 5,891,134 A | 4/1999 | Goble et al. | |
| 5,904,651 A | 5/1999 | Swanson et al. | |
| 5,908,415 A | 6/1999 | Sinofsky | |
| 5,931,834 A | 8/1999 | Murphy-Chutorian et al. | |
| 5,938,660 A | 8/1999 | Swartz et al. | |
| 5,947,959 A | 9/1999 | Sinofsky | |
| 5,967,984 A | 10/1999 | Chu et al. | |
| 5,971,983 A | 10/1999 | Lesh | |
| 5,995,875 A | 11/1999 | Blewett et al. | |
| 6,004,269 A | 12/1999 | Crowley et al. | |
| 6,012,457 A | 1/2000 | Lesh | |
| 6,024,740 A | 2/2000 | Lesh et al. | |
| 6,056,744 A | 5/2000 | Edwards | |
| 6,064,902 A | 5/2000 | Haissaguerre et al. | |
| 6,071,279 A | 6/2000 | Whayne et al. | |
| 6,071,281 A | 6/2000 | Burnside et al. | |
| 6,071,282 A | 6/2000 | Fleischman | |
| 6,071,302 A | 6/2000 | Sinofsky et al. | |
| 6,086,581 A | 7/2000 | Reynolds et al. | |
| 6,090,084 A | 7/2000 | Hassett et al. | |
| 6,099,514 A | 8/2000 | Sharkey et al. | |
| 6,102,905 A | 8/2000 | Baxter et al. | |
| 6,117,071 A | 9/2000 | Ito et al. | |
| 6,117,101 A | 9/2000 | Diederich et al. | |
| 6,120,496 A | 9/2000 | Whayne et al. | |
| 6,146,379 A | 11/2000 | Fleischman et al. | |
| 6,159,203 A | 12/2000 | Sinofsky | |

(56) References Cited

U.S. PATENT DOCUMENTS

| | | |
|---|---|---|
| 6,161,543 A | 12/2000 | Cox et al. |
| 6,164,283 A | 12/2000 | Lesh |
| 6,179,835 B1 | 1/2001 | Panescu et al. |
| 6,214,002 B1 | 4/2001 | Fleischman et al. |
| 6,217,510 B1 | 4/2001 | Ozawa et al. |
| 6,235,025 B1 | 5/2001 | Swartz et al. |
| 6,237,605 B1 | 5/2001 | Vaska et al. |
| 6,240,231 B1 | 5/2001 | Ferrera et al. |
| 6,245,064 B1 | 6/2001 | Lesh et al. |
| 6,251,092 B1 | 6/2001 | Qin et al. |
| 6,251,109 B1 | 6/2001 | Hassett et al. |
| 6,254,599 B1 | 7/2001 | Lesh et al. |
| 6,270,492 B1 | 8/2001 | Sinofsky |
| 6,305,378 B1 | 10/2001 | Lesh |
| 6,312,427 B1 | 11/2001 | Berube et al. |
| 6,314,962 B1 | 11/2001 | Vaska et al. |
| 6,325,797 B1 | 12/2001 | Stewart et al. |
| 6,352,531 B1 | 3/2002 | O'Connor et al. |
| 6,383,151 B1 | 5/2002 | Diederich et al. |
| 6,394,949 B1 | 5/2002 | Crowley et al. |
| 6,416,511 B1 | 7/2002 | Lesh et al. |
| 6,423,055 B1 | 7/2002 | Farr et al. |
| 6,423,058 B1 | 7/2002 | Edwards et al. |
| 6,471,697 B1 | 10/2002 | Lesh |
| 6,485,485 B1 | 11/2002 | Winston et al. |
| 6,500,174 B1 | 12/2002 | Maguire et al. |
| 6,502,576 B1 | 1/2003 | Lesh |
| 6,503,247 B2 | 1/2003 | Swartz et al. |
| 6,514,249 B1 | 2/2003 | Maguire et al. |
| 6,522,933 B2 | 2/2003 | Nguyen |
| 6,544,262 B2 | 4/2003 | Fleischman |
| 6,547,780 B1 | 4/2003 | Sinofsky |
| 6,554,794 B1 | 4/2003 | Mueller et al. |
| 6,558,375 B1 | 5/2003 | Sinofsky et al. |
| 6,562,020 B1 | 5/2003 | Constantz et al. |
| 6,572,609 B1 | 6/2003 | Farr et al. |
| 6,579,278 B1 | 6/2003 | Bencini |
| 6,579,285 B2 | 6/2003 | Sinofsky |
| 6,582,536 B2 | 6/2003 | Shimada |
| 6,605,055 B1 | 8/2003 | Sinofsky |
| 6,605,084 B2 | 8/2003 | Acker et al. |
| 6,626,900 B1 | 9/2003 | Sinofsky et al. |
| 6,635,054 B2 | 10/2003 | Fjield et al. |
| 6,648,875 B2 | 11/2003 | Simpson et al. |
| 6,669,655 B1 | 12/2003 | Acker et al. |
| 6,676,656 B2 | 1/2004 | Sinofsky |
| 6,679,873 B2 | 1/2004 | Rabiner et al. |
| 6,702,780 B1 | 3/2004 | Gilboa et al. |
| 6,771,996 B2 | 8/2004 | Bowe et al. |
| 6,896,673 B2 | 5/2005 | Hooven |
| 6,907,298 B2 | 6/2005 | Smits et al. |
| 6,916,306 B1 | 7/2005 | Jenkins et al. |
| 6,932,809 B2 | 8/2005 | Sinofsky |
| 6,942,657 B2 | 9/2005 | Sinofsky et al. |
| 6,953,457 B2 | 10/2005 | Farr et al. |
| 6,997,924 B2 | 2/2006 | Schwartz et al. |
| 7,207,984 B2 | 4/2007 | Farr et al. |
| 7,285,117 B2 * | 10/2007 | Krueger et al. ............... 606/34 |
| 7,357,796 B2 | 4/2008 | Farr et al. |
| 7,935,108 B2 | 5/2011 | Baxter et al. |
| 8,025,661 B2 | 9/2011 | Arnold et al. |
| 2001/0030107 A1 | 10/2001 | Simpson |
| 2002/0019627 A1 | 2/2002 | Maguire et al. |
| 2002/0029062 A1 | 3/2002 | Satake |
| 2002/0065512 A1 | 5/2002 | Fjield et al. |
| 2002/0091383 A1 | 7/2002 | Hooven |
| 2002/0107511 A1 | 8/2002 | Collins et al. |
| 2002/0115995 A1 | 8/2002 | Lesh et al. |
| 2002/0120264 A1 | 8/2002 | Crowley et al. |
| 2002/0183729 A1 | 12/2002 | Farr et al. |
| 2002/0183739 A1 | 12/2002 | Long |
| 2003/0050632 A1 | 3/2003 | Fjield et al. |
| 2003/0065307 A1 | 4/2003 | Lesh |
| 2003/0069620 A1 | 4/2003 | Li |
| 2003/0111085 A1 | 6/2003 | Lesh |
| 2003/0120270 A1 | 6/2003 | Acker |
| 2003/0144657 A1 | 7/2003 | Bowe et al. |
| 2003/0158550 A1 | 8/2003 | Ganz et al. |
| 2003/0171746 A1 | 9/2003 | Fleischman |
| 2004/0006333 A1 | 1/2004 | Arnold et al. |
| 2004/0054360 A1 | 3/2004 | Schwartz et al. |
| 2004/0059397 A1 | 3/2004 | Sinofsky et al. |
| 2004/0122290 A1 | 6/2004 | Irion et al. |
| 2005/0038419 A9 | 2/2005 | Arnold et al. |
| 2005/0065504 A1 | 3/2005 | Melsky et al. |
| 2005/0288654 A1 | 12/2005 | Nieman et al. |
| 2006/0253113 A1 | 11/2006 | Arnold et al. |
| 2007/0078451 A1 | 4/2007 | Arnold et al. |
| 2008/0039746 A1 | 2/2008 | Hissong et al. |
| 2008/0108870 A1 | 5/2008 | Wiita et al. |
| 2008/0195088 A1 | 8/2008 | Farr et al. |
| 2009/0221996 A1 | 9/2009 | Lesh et al. |
| 2009/0221997 A1 | 9/2009 | Arnold et al. |
| 2009/0275934 A1 | 11/2009 | Baxter et al. |
| 2009/0299354 A1 | 12/2009 | Melsky et al. |
| 2009/0326320 A1 | 12/2009 | Sinofsky et al. |
| 2011/0082449 A1 | 4/2011 | Melsky et al. |
| 2011/0082450 A1 | 4/2011 | Melsky et al. |
| 2011/0082451 A1 | 4/2011 | Melsky |
| 2011/0082452 A1 | 4/2011 | Melsky et al. |
| 2011/0245822 A1 | 10/2011 | Baxter et al. |
| 2011/0245828 A1 | 10/2011 | Baxter et al. |

FOREIGN PATENT DOCUMENTS

| | | |
|---|---|---|
| EP | 0292621 | 11/1988 |
| EP | 0292695 | 11/1988 |
| EP | 0299448 | 1/1989 |
| EP | 0311458 | 4/1989 |
| EP | 0437181 | 7/1991 |
| EP | 0437183 | 7/1991 |
| EP | 0439629 | 8/1991 |
| EP | 0598984 | 6/1994 |
| EP | 0792664 | 9/1997 |
| EP | 1072231 | 1/2001 |
| EP | 1331893 | 12/2004 |
| FR | 2798371 A | 3/2001 |
| JP | 2003-210028 A | 7/2003 |
| JP | 2004-065076 A | 3/2004 |
| WO | WO 9217243 | 10/1992 |
| WO | WO 9306888 | 4/1993 |
| WO | WO 9319680 | 10/1993 |
| WO | WO 9325155 | 12/1993 |
| WO | WO 9417434 | 8/1994 |
| WO | WO 9426184 | 11/1994 |
| WO | WO 9607451 | 3/1996 |
| WO | WO 9634646 | 11/1996 |
| WO | WO 9640342 | 12/1996 |
| WO | WO 9737714 | 10/1997 |
| WO | WO 00/67656 | 11/2000 |
| WO | WO 00/67832 | 11/2000 |
| WO | WO 01/03599 A2 | 1/2001 |
| WO | WO 0113812 | 3/2001 |
| WO | WO 01/64123 | 9/2001 |
| WO | WO 02/096479 | 12/2002 |
| WO | WO 03090835 | 11/2003 |
| WO | WO 2004-110258 | 12/2004 |

OTHER PUBLICATIONS

Chevalier, P. et al. "Thoracoscopic Epicardial Radiofrequency Ablation for Vagal Atrial Fibrillation in Dogs" PACE, 1999, 22: 880-886.

Froelich, J. et al. "Evaluation of a Prototype Steerable Angioscopic Laser Catheter in a Canine Model: A Feasibility Study" Cardiovasc Intervent Radiol, 1993 16: 235-238.

Fujimura, O. et al. "Direct in Vivo Visualization of Right Cardiac Anatomy by Fiberoptic Endoscopy" Angiology; 1995, 46 (3): 201-208.

Fujimura, O. et al. "Direct in Vivo Visualization of Right Cardiac Anatomy by Fiberoptic Endoscopy: Observation of Radiofrequency-Induced Acute Lesions Around the Ostium of the Coronary Sinus" European Heart J., 1994, 15: 534-540.

(56) References Cited

OTHER PUBLICATIONS

Gamble, W. and Innis, R. "Experimental Intracardiac Visualization" NEJM, 1967, 276(25): 1397-1403.

Hirao, K. et al. "Transcatheter Neodymium-Yttrium-Aluminum-Garnet Laser Coagulation of Canine Ventricle Using a Balloon-Tipped Cardioscope" Jpn Circ J., 1997, 61: 695-703.

Keane, D. et al. "Pulmonary Vein Isolation for Atrial Fibrillation" Rev Cardiovasc Med., 2002, 3(4): 167-175.

Kuo, C. et al. "In Vivo Angioscopic Visualization of Right Heart Structure in Dogs by Means of a Balloon-Tipped Fiberoptic Endoscope: Potential Role in Percutaneous Ablative Procedures." American Heart J., 1994, 127: 187-197.

Nakagawa, H. et al. "Cardioscopic Catheter Ablation with Noncontact, Pulsed Nd:YAG Laser Using Saline Inflated Balloon Catheter," Presentation JACC 1998; 31: 118A-119A.

Obelienius, V. et al. "Transvenous Ablation of the Atrioventricular Conduction System by Laser Irradiation Under Endoscopic Control" Lasers in Surgery Medicine, 1985, 5: 469-474.

Roggan, A., et al. "Optical Properties of Circulating Human Blood in the Wavelength Range 400-2400 nm" J Biomedical Optics, 1999, 4(1): 36-46.

Saliba, W. et al. "Circumferential Ultrasound Ablation for Pulmonary Vein Isolation: Analysis of Acute and Chronic Failures" J Cardiovascular Electrophysiology, 2002, 13(10): 957-961.

Shure, D. et al. "Identification of Pulmonary Emboli in the Dog: Comparison of Angioscopy and Perfusion Scanning" Circulation, 1981, 64(3): 618-621.

Shure, D., et al. "Fiberoptic Angioscopy: Role in the Diagnosis of Chronic Pulmonary Arterial Obstruction" Ann Int Med., 1985, 103: 844-850.

Tanabe, T. et al. "Cardiovascular Fiberoptic Endoscopy: Development and Clinical Application" Surgery, 1980, 87(4): 375-379.

Tanaka, K. et al., "Endoscopy-Assisted Radiofrequency Ablation Around the Coronary Sinus Ostium in Dogs: Its Effects on Atrioventricular Nodal Properties and Ventricular Response During Atrial Fibrillation," Journal of Cardiovascular Electrophysiology, vol. 7, No. 11, Nov. 1996, pp. 1063-1073.

Uchida, Y. et al. "Fiberoptic Angioscopy of Cardiac Chambers, Valves, and Great Vessels Using a Guiding Balloon Catheter in Dogs." American Heart J., 1998, 115(6): 1297-1302.

Uchida, Y. et al. "Percutaneous Pulmonary Angioscopy Using a Guiding Balloon Catheter" Clin. Cardiol., 1988, 11: 143-148.

Vanermen, H. et al. "Minimally Invasive Video-Assisted Mitral Valve Surgery: From Port-Access Towards a Totally Endoscopic Procedure" J Card Surg., 2000, 15: 51-60.

Yamamoto, N et al. "Nonfluoroscopic Guidance for Catheter Placement into the Coronary Sinus under Direct Vision Using a Balloon-Tipped Cardioscope" PACE, 1998; 21: 1724-1729.

Sinus under Direct Vision Using a Balloon-Tipped Cardioscope PACE, 1998; 21: 1724-1729.

\* cited by examiner

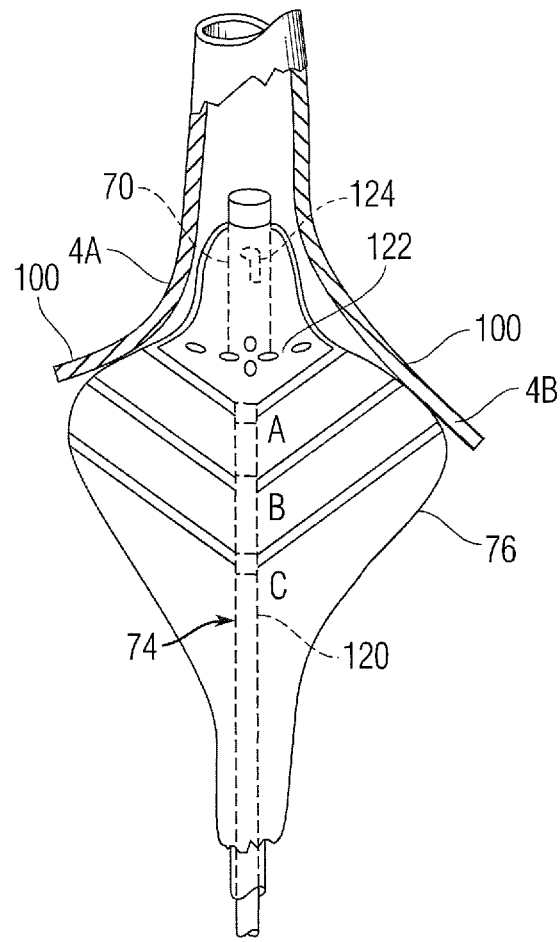
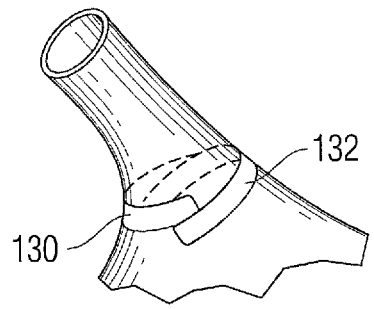
Fig. 9B
Fig. 9A

SYSTEM AND METHOD FOR VISUALIZING TISSUE DURING ABLATION PROCEDURES

RELATED APPLICATION(S)

This application is a continuation-in-part of U.S. patent application Ser. No. 10/865,558, filed on Jun. 10, 2004, entitled "Guided Cardiac Ablation Catheters," which claims priority of U.S. Provisional Patent Application Ser. No. 60/477,374, filed Jun. 10, 2003 and is a continuation-in part of U.S. patent application Ser. No. 10/357,156, filed Feb. 3, 2003, which is a continuation-in-part of U.S. patent application Ser. No. 09/924,393, filed on Aug. 7, 2001.

U.S. patent application Ser. No. 10/865,558 is also a continuation-in-part of U.S. patent application Ser. No. 10/674,114, filed Sep. 29, 2003, which is a continuation of U.S. patent application Ser. No. 09/616,275 filed Jul. 14, 2000, now U.S. Pat. No. 6,626,900, which is a continuation-in-part of U.S. patent application Ser. No. 09/602,420 filed Jun. 23, 2000, now U.S. Pat. No. 6,572,609, which is a continuation-in-part of U.S. patent application Ser. No. 09/357,355, filed on Jul. 14, 1999, now U.S. Pat. No. 6,423,055 issued Jul. 22, 2002.

The teachings of all of these prior related patents and applications are hereby expressly incorporated herein by reference.

BACKGROUND

Atrial fibrillation (AF or afib) is a cardiac arrhythmia (abnormal heart rhythm) that involves the two upper chambers (atria) of the heart. It can often be identified by taking a pulse and observing that the heartbeats do not occur at regular intervals, but a conclusive indication of AF is the absence of P waves on an electrocardiogram (ECG). AF is the most common arrhythmia; risk increases with age, with 8% of people over 80 having AF. In AF, the normal electrical impulses that are generated by the sinoatrial node are overwhelmed by disorganized electrical impulses that originate in the atria and pulmonary veins, leading to conduction of irregular impulses to the ventricles that generate the heartbeat. The result is an irregular heartbeat which may occur in episodes lasting from minutes to weeks, or it could occur all the time for years. The natural tendency of AF is to become a chronic condition.

Patients with AF usually have a significantly increased risk of stroke (up to about 7 times that of the general population). Stroke risk increases during AF because blood may pool and form clots in the poorly contracting atria and especially in the left atrial appendage (LAA). The level of increased risk of stroke depends on the number of additional risk factors. If the AF patient has none, the risk of stroke is similar to that of the general population. However, many patients do have additional risk factors and AF is a leading cause of stroke.

Atrial fibrillation may be treated with medications which either slow the heart rate or revert the heart rhythm back to normal. Synchronized electrical cardioversion may also be used to convert AF to a normal heart rhythm. Surgical and catheter-based therapies may also be used to prevent recurrence of AF in certain individuals. People with AF are often given anticoagulants such as warfarin to protect them from stroke.

In patients with AF where rate control drugs are ineffective and it is not possible to restore sinus rhythm using cardioversion, non-pharmacological alternatives are available. For example, to control rate it is possible to destroy the bundle of cells connecting the upper and lower chambers of the heart—the atrioventricular node—which regulates heart rate, and to implant a pacemarker instead. A more complex technique, which avoids the need for a pacemaker, involves ablating groups of cells near the pulmonary veins where atrial fibrillation is thought to originate, or creating more extensive lesions in an attempt to prevent atrial fibrillation from establishing itself.

Ablation is a technique that has shown some promise for cases of recurrent AF that are unresponsive to conventional treatments. Radiofrequency ablation (RFA) uses radiofrequency energy to destroy abnormal electrical pathways in heart tissue. Other energy sourses include laser, cryothermy, and high intensity ultrasound. The energy emitting probe is placed into the heart through a catheter inserted into veins in the groin or neck. Electrodes that can detect electrical activity from inside the heart are also inserted, and the electrophysiologist uses these to "map" an area of the heart in order to locate the abnormal electrical activity before eliminating the responsible tissue.

Most AF ablations consist of isolating the electrical pathways from the pulmonary veins (PV), which are located on the posterior wall of the left atrium. All other veins from the body (including neck and groin) lead to the right atrium, so in order to get to the left atrium the catheters must get across the atrial septum. This can be done by piercing a small hole in the septal wall. This is called a transseptal approach. Once in the left atrium, the physician may perform an abaltion procedure to electrically isolate the PVs from the left atrium.

Currently, when laser energy has been applied to a region of tissue at an ostium of the PV there is little to no visible change to that region of tissue when viewed through an endoscope thereby presenting the problem of distinguishing treated tissue (e.g., lesion) from de novo tissue.

The lesions are not visible for various reasons. For example, the ablation energy in these procedures typically penetrates deeply into the atrial tissue to create the lesion while leaving the endocardial surface relatively undamaged. Additionally, color video cameras are often not sensitive enough to discriminate the subtle color changes that distinguish treated and untreated tissue. Also, the light levels delivered to the site are limited since they typically travel to the treatment site via a small optical fiber thereby further hindering the ability of video cameras to visualize these distinctions.

Thus, there remains a need in the art for systems and methods configured to accurately and efficiently discriminate lesions from de novo tissue.

SUMMARY

Systems for distinguishing lesions from de novo tissue during ablation procedures are provided herein. In use, the system is configured to compare absorbance/reflectivity data at distinct wavelengths to determine if an area in question is lesion or de novo tissue. Additionally, the system can include a video monitor for real-time imaging of a treatment area with false-coloring applied to those areas determined to be lesions. Thus, the presently disclosed system discriminates between lesion and de novo tissue in an accurate and efficient manner thereby increasing the safety of cardiac tissue ablation procedures.

Various embodiments of a tissue visualization system are provided. In one such embodiment, the system includes an illumination source configured to illuminate tissue, and a reflectivity sensor (e.g., a fiber-optic endoscope) sized and shaped to be slidably disposed within a lumen of a catheter, and configured to capture reflected light from an area of tissue. The system also includes an imaging module in communication with the reflectivity sensor, and configured to receive reflectivity/absorbance data from the reflectivity sensor so as to detect a first amount of light reflected by the area of tissue at a first, predetermined waveband and a second amount of light reflected by the area of tissue at a second, predetermined waveband. The system further includes a processor in communication with the imaging module, and configured to compare the first amount of light relative to the second amount of light, and further configured to classify the area of tissue as a lesion or as de novo tissue if the first amount of light is less than or greater than the second amount of light, respectively.

In one embodiment, the first, predetermined waveband is centered at about 550 nm, and the second, predetermined waveband is centered at about 560 nm. Various wavebands can be utilized. For example, each waveband can be about 40 nm wide.

The imaging module can include a video camera having a plurality of video chips with at least a first and a second video chip configured to generate a first image and a second image based on the first predetermined wavelength band and the second predetermined wavelength band, respectively. The chips can be configured as such by placing the first and second chips into communication with first and a second bandpass filters, respectively. The video camera can further include a third video chip configured to generate a third image based on a third predetermined wavelength band which is selected from another desired waveband, e.g., a red waveband or a blue waveband.

In one embodiment, the processor is configured to generate a combined image from the first image and the second image generated by the first and second video chips, respectively. The processor can also be configured to apply a false coloring indicative of a treatment status (e.g., a lesion) to at least a portion of the combined image. The system can also include a video monitor configured to display a real-time view of the combined image.

Various embodiments of a cardiac ablation system are also provided herein. In one embodiment, the ablation system includes an elongate catheter having a lumen extending therethrough and an energy emitter slidably disposed within the lumen. The ablation system also includes a visualization module configured to irradiate an area of tissue with light from within the lumen so as to generate reflectivity data, and further configured to detect a first amount of light reflected by the area at a first, predetermined waveband and a second amount of light reflected at a second, predetermined waveband. The ablation system also includes a processor in communication with the visualization module, and configured to compare the first amount of light to the second amount of light, and further configured to determine if the tissue area is a lesion based on the comparison. In one embodiment, the first, predetermined waveband is centered at about 550 nm, and the second predetermined waveband is centered at about 560 nm.

Various energy emitters can be utilized. In one embodiment, the energy emitter is configured to deliver rings, partial rings, or spots of ablative energy to the treatment area. Also, various types of catheters can be utilized. In one embodiment, the catheter is sized and configured to provide access to an ostium of a pulmonary vein (e.g., for use in the treatment of atrial fibrillation).

Additionally, various methods of distinguishing lesions from de novo tissue are also provided herein. In one embodiment, the method includes irradiating an area of tissue with light, and comparing a first amount of light reflected by the area at a first, predetermined waveband to a second amount of light reflected by the area at a second, predetermined waveband. The method further includes classifying the area as a lesion or as de novo tissue if the first amount of light is less than or greater than the second amount of light, respectively. In one embodiment, the first, predetermined waveband is centered at about 550 nm, and the second, predetermined waveband is centered at about 560 nm.

The method can further include displaying a real-time image of the tissue area with a type of false-coloring (e.g., coloring, shading, brightening) indicative of a treatment status (e.g., lesion or de novo tissue). The method can also include ablating tissue classified as de novo tissue.

Additionally, various embodiments of a method for treating atrial fibrillation are provided herein. In one embodiment, the method includes delivering a distal portion of an ablation catheter to a position adjacent an ostium of a pulmonary vein, and irradiating a partial ring of tissue along the ostium via a reflectivity sensor slidably disposed within a lumen of the ablation catheter. The method also includes comparing a first amount of light reflected by a spot or partial ring of tissue at a first, predetermined waveband to a second amount of light reflected by the spot or partial ring of tissue at a second, predetermined waveband, and classifying the observed tissue region as a lesion or as de novo tissue if the first amount of light is less than or greater than the second amount of light, respectively. The method further includes ablating the observed tissue region if classified as de novo tissue.

The method can further include repeating the irradiating, comparing, classifying, and ablating steps for each of a plurality of target tissue regions thereby providing a substantially continuous lesion around the ostium of the pulmonary vein.

The method can further include displaying a real-time image of the ostium of the pulmonary vein on a video monitor. For example, the image can be taken along a longitudinal axis of the catheter. In one embodiment, the real-time image can indicate target regions as lesions or as de novo tissue. For example, those areas designated as lesions can be indicated by a type of false coloring (e.g., coloring, shading, brightening, etc.).

BRIEF DESCRIPTION OF THE DRAWINGS

The invention will be more fully understood from the following detailed description taken in conjunction with the accompanying drawings, in which like reference numerals designate like parts throughout the figures, and wherein:

FIG. 9A is a representation of various target regions capable of being targeted by an embodiment of an energy emitter slidably disposed within an ablation catheter;

FIG. 9B is a schematic representation of overlapping lesions encircling an ostium of a pulmonary vein.

DETAILED DESCRIPTION

Systems for distinguishing cardiac lesions from untreated tissue are provided herein. The systems can also provide real-time video imaging of the cardiac treatment site indicative of treated and untreated tissue regions. For example, the system can be utilized in treating atrial fibrillation where a plurality of partial or complete ring-like or "spot" tissue regions extending along various portions of an ostium of a pulmonary vein are ablated to provide a continuous lesions surrounding the vein. In such a procedure, the systems can determine which regions have been treated, which regions have not been treated, which regions have been treated but are in need of further treatment, etc. As such, the various embodiments of the visualization and imaging systems can be incorporated into and/or used in conjunction with an ablation catheter configured to specifically target and ablate a region in need of treatment.

Figure 1:
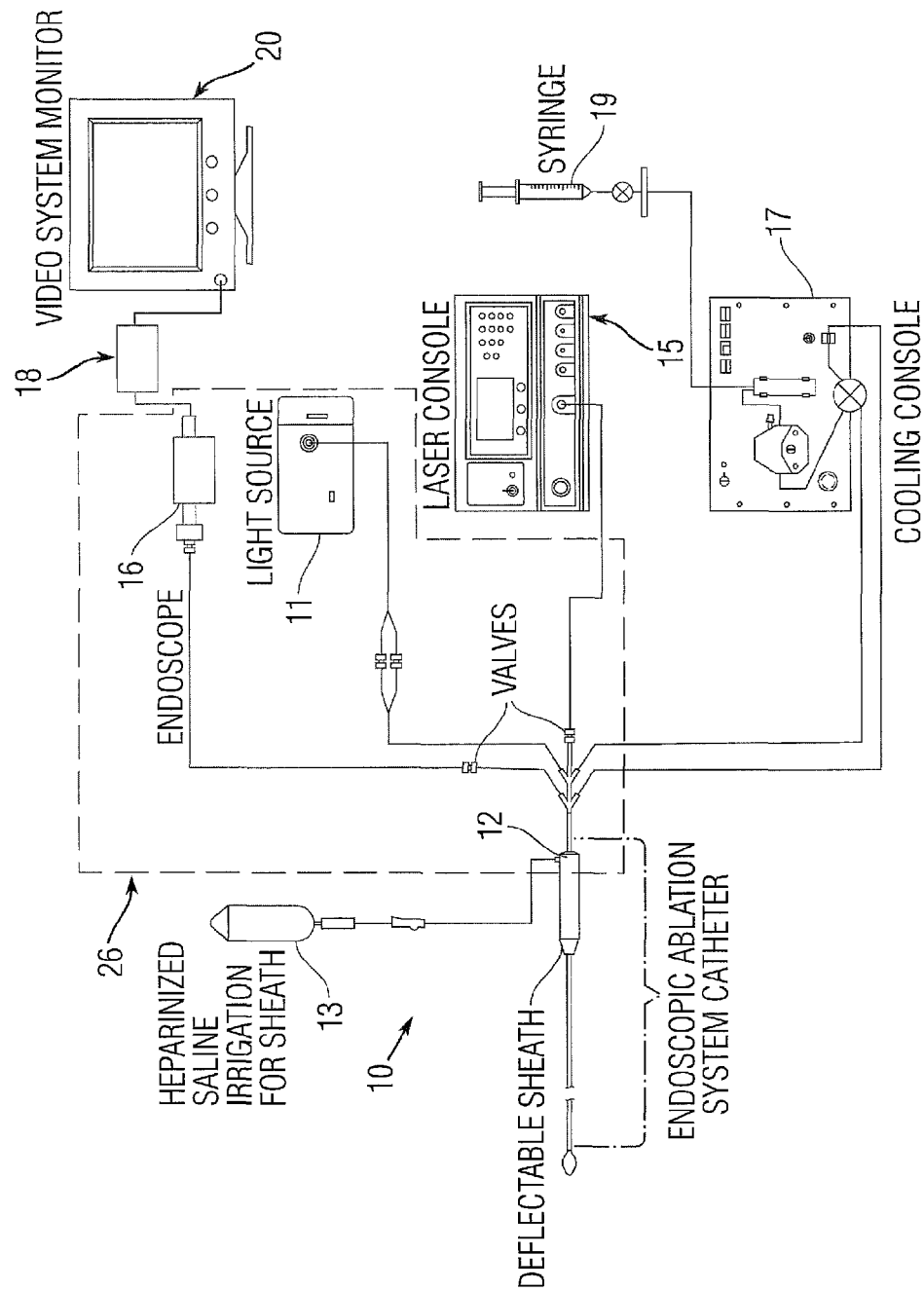
FIG. 1 is a representation of various components of an embodiment of the presently disclosed system.

FIG. 1 provides a general representation of the presently disclosed visualization and imaging system 10. As shown, the system 10 typically includes an illumination source 11 configured to irradiate at least a portion of a tissue area with light, and a reflectivity sensor 12 configured to detect resulting absorbance/reflectivity data. The system 10 also includes an imaging module 16 in communication with the reflectivity sensor 12, and configured to generate a plurality of images which, taken together, can distinguish lesions from untreated, de novo tissue. That is, the imaging module 16 can be specifically tuned to those wavebands which exhibit subtle differences between treated and untreated tissue. Typically, the reflectivity sensor 12 can play a role in detecting and/or transmitting reflectivity/absorbance data from the reflected light to the imaging module 16. Thus, the reflectivity sensor 12, illumination source 11, and the imaging module 16 can be considered to be components in a visualization module 26 of the system 10.

The system 10 can further include a processor 18 configured to receive data from the imaging module 16, compare such absorbance/reflectivity data of various wavebands, and utilize these comparisons as well as various other levels of analysis for the purpose of classifying the area as lesion or de novo tissue. The processor 18 can also generate a combined image of the tissue by combining a plurality of waveband specific images generated by the imaging module 16. Additionally, the processor 18 can apply some degree of false-coloring (e.g., coloring, shading, brightening, etc.) indicative of treatment status (e.g., lesion or de novo) to the combined image. The system 10 can also include a video monitor 20 configured to provide a real-time view of the combined image as generated by the processor 18. Thus, the system 10 can provide real-time information indicative of lesions and identifying those areas in need of treatment.

As shown, the system 10 can also include various other optional components. For example, the system 10 can include a mechanism 13 for providing heparinized saline irrigation for a sheath of an endoscopic ablation catheter system (discussed further below), a laser console 15 for generating ablation energy, a cooling console 17, and/or a syringe 19 for delivering fluid (e.g., $D_2O$) to an inflation balloon of the catheter system. Those skilled in the art will appreciate that various alternative or additional components are within the spirit and scope of the present disclosure.

Various embodiments of a reflectivity sensor 12 are within the spirit and scope of the present disclosure. In general, the reflectivity sensor 12 can be any component which is sized and shaped so as to be delivered to a treatment site (e.g., via a cardiac catheter) and further configured to detect light reflected by the target tissue site, and also configured to transit reflectivity/absorbance data to the imaging module 16. In an exemplary embodiment, the reflectivity sensor is a fiber-optic endoscope.

Figure 2:
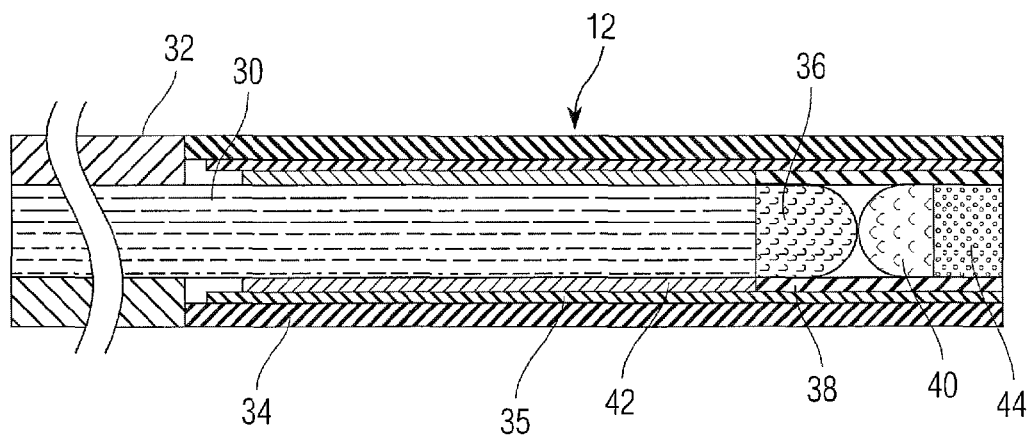
FIG. 2 is a side view of an exemplary embodiment of a reflectivity sensor of the presently disclosed system.

FIG. 2 shows an exemplary embodiment of the fiber-optic endoscope with enhanced field of view. The endoscope 12 includes a fiber bundle 30 within a protective polyimide tube 32 coupled to distal stainless steel tube 34 in which the field-enhancing optics are disposed. Within the distal tube 34, an imaging lens 36, and an objective lens 40 are situated, together with a centering and connecting tubes (e.g., tubes 35, 42) as may be needed to secure the lenses 36, 40 in place.

The endoscope 12 can have a wide field of view even while it is immersed in liquid. For example, in use, the endoscope 12 will typically be immersed in either physiological saline (as is typically found in the inner lumen of a catheter) or deuterium oxide which is one preferred medium for filling a projection balloon (detailed below) coupled to a catheter. Both of these liquids have essentially the same index of refraction.

Referring again to FIG. 2, the lens system can be configured to provide the desired field of view in such liquid environments. That is, the lens system includes two plano-convex lenses 36, 38 arranged as shown along with an apertured window 44. High index of refraction materials are preferably used for the lenses 36, 38. Suitable materials include sapphire, cubic zirconia, or high index glass materials. All these materials are readily available as small diameter spheres with optical quality surfaces. The spheres can be made into hemispheres and the diameter of the hemispheres are reduced using common lens grinding technology. The aperture can be constructed by metalizing one surface of flat glass plate. The central aperture hole is created by masking the flat glass before the metallization or removing the metallization with a laser.

The lens elements can be formed of various materials and/or can have various dimensions. For example, sample specifications for the lens elements are as follows:

TABLE 1

Lens Specifications

| Element Name | Material | Spherical Radius | Overall Diameter | Center thickness |
|---|---|---|---|---|
| Object Lens | Cubic Zirconia or high index glass | 0.200 mm | 0.400 mm | 0.244 mm |
| Image Lens | Saphire or high index glass | 0.300 mm | 0.400 mm | 0.187 mm |
| Aperture Window 0.060 mm dia. | Schott B270 Grade A glass | Flat on both Faces | 0.400 mm | 0.125 mm |

The lens system can be configured to have a field of view of slightly larger than about 110° when immersed in water, an f number of about 2.5, and a depth of field that provides acceptable focus over a range of object distances from about 13 mm to about 40 mm. Acceptable focus is that degree of focus that results in minimum resolvable spot diameters that are close in size to about 5 microns, which is the size of the individual fibers in the image bundle of the endoscope.

The lens elements can be assembled so the spherical surfaces touch and therefore the elements are self-locating when assembled in a small lens cell tube 38 with an inner diameter just slightly larger than the outer diameter of the lens elements. Once the lens cell is fabricated it is attached to the image bundle using techniques common to those skilled in the art. The general assembly can use precise diameter tubes of polyimide whose dimensions can be controlled very precisely and whose wall thicknesses can be made very thin.

The ability have a field of view greater than about 50 degrees (and, preferably, in some applications, greater than about 70 degrees, or about 90 degrees) can be beneficial because of the geometry of the heart and the ablation elements capable of being utilized in combination with the reflectivity sensor 12. For example, visualization of an ostium of a pulmonary vein through a transparent liquid filled balloon typically requires a wide field of view. Moreover, an energy element and/or various expandable balloon components of an ablation catheter, detailed below, must be short due to the limited space available within the atrial chamber. Such factors combine to require the endoscope 12 to be positioned close to the ostium of the pulmonary vein thereby requiring a wide field of view to visualize the target region and the endoscope's and/or catheter's position relative to the target region.

Referring back to FIG. 1, the system 10 also includes an imaging module 16 in communication with the reflectivity sensor 12, and configured to receive absorbance and/or reflectivity signals/data from the sensor 12. In an exemplary embodiment, the imaging module 16 can be specifically tuned to detect amounts of light reflected by the tissue at a plurality of predetermined wavebands which are selected due to their ability to distinguish between a lesion and de novo tissue. Additionally, the imaging module 16 can be configured to generate a plurality of images based on these plurality of predetermined wavebands. These images are then assembled into a combined image by a processor, detailed below, so as to provide a real time view of the treatment site with indications as to which tissue areas are lesions and which areas are in need of further treatment.

Figure 3:
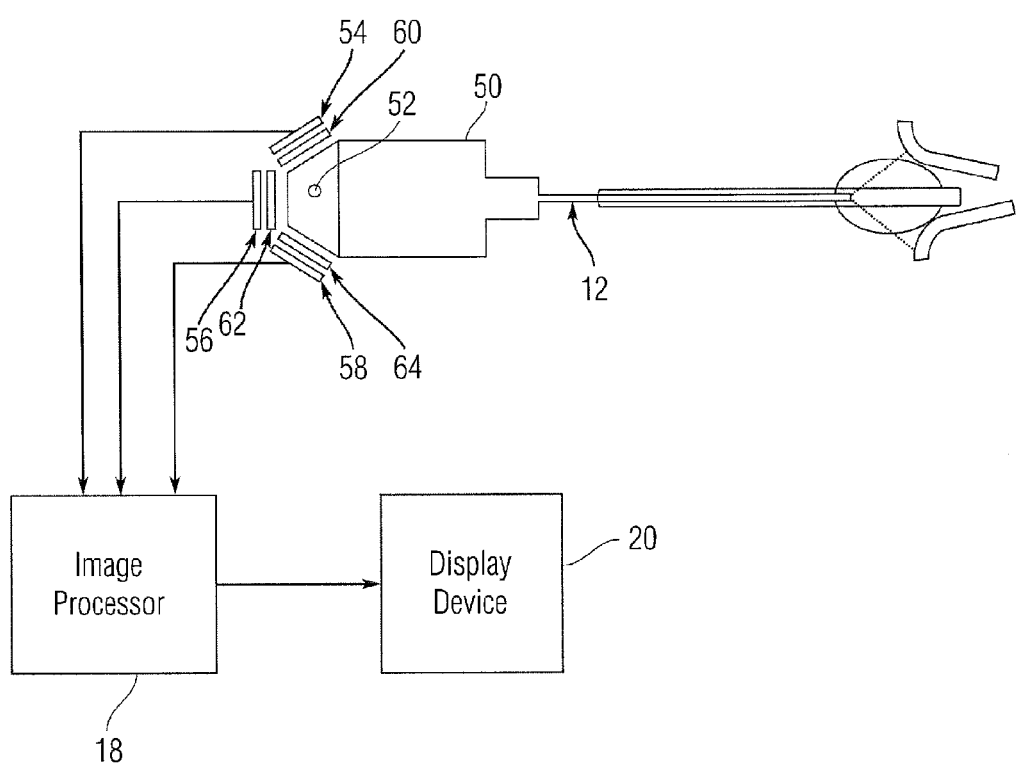
FIG. 3 is a representation of various components of an exemplary embodiment of an imaging module of the presently disclosed system.

FIG. 3 is a schematic representation of various components of an exemplary embodiment of the imaging module 16. As shown, the imaging module 16 includes an image forming optics component 50 which is configured to receive reflectivity/absorbance data from the reflectivity sensor 12, as represented by an arrow between these components 12, 50, and transmit the data into an image splitter 52. The image splitter 50 can split the image into any number of images as desired.

The image module 16 further includes a plurality of video chips 54, 56, 58 for generating a corresponding number of individual images which can later be combined by a processor of the system (detailed below). Typically, the image splitter 52 will split the image into a number of images corresponding to the number of video chips. Thus, in the exemplary embodiment of FIG. 3, the image splitter 52 splits the image into first, second, and third images directed towards first, second, and third video chips 54, 56, 58, respectively. Those skilled in the art will appreciate that any number and/or type of video chips are within the spirit and scope of the present disclosure.

In distinguishing lesions from de novo tissue, at least two of the video chips 54, 56 are specifically tailored towards specific wavebands such that an amount of light reflected at first and second wavebands can be compared relative to one another. As detailed below, the wavebands can be selected such that this comparison can indicate whether or not the target area is lesion or de novo tissue.

The video chips 54, 56, 58 can be tailored towards specific predetermined wavebands in various manners. For example, each chip 54, 56, 58 can be in communication with a distinct bandpass filter 60, 62, 64 with each filter 60, 62, 64 being tailored to a specific waveband of a certain width and centered at a specific wavelength. Those skilled in the art will appreciate that various types of such filters 60, 62, and 64 are within the spirit and scope of the present disclosure.

As indicated, at least two video chips, for example, the first and second video chips 54, 56, can be tailored towards first and second predetermined wavebands, respectively, with the resulting data indicative of whether the tissue area is a lesion or de novo tissue. The predetermined wavebands can be determined by careful inspection of experimental absorbance/reflectivity data.

Figure 4:
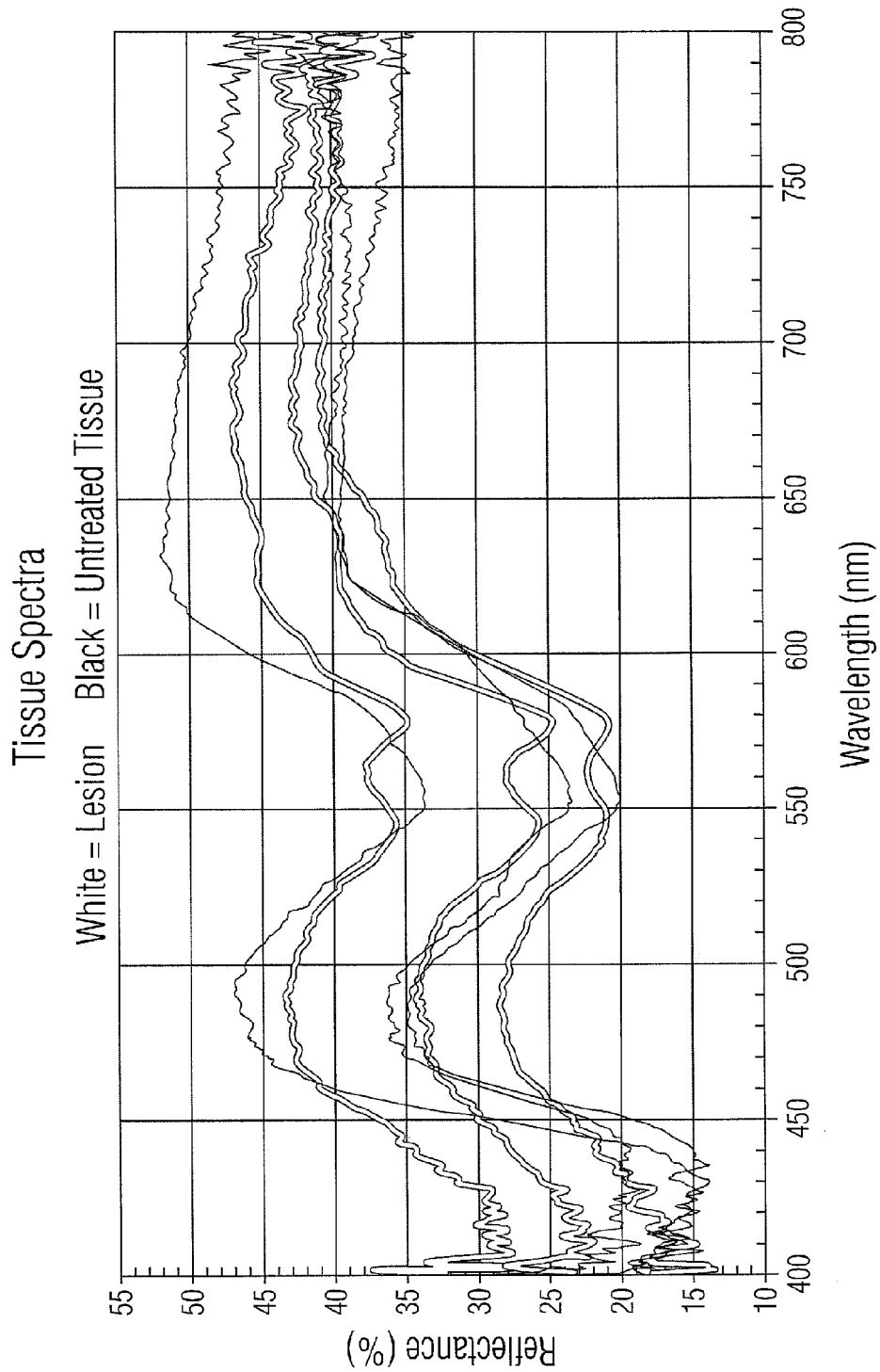
FIG. 4 is a graph of reflectance versus wavelength data for various lesion and de novo tissue samples.

FIG. 4 provides several visible light spectra collected for untreated tissue (black lines) and lesions (gray lines). Inspection of these spectra revealed various characteristics of lesions and untreated tissue. First, the general shape of the spectra are similar for both lesion and untreated tissue. That is, both lesion and untreated tissue reflect light readily in the waveband of about 425 nm to about 500 nm, and also readily reflect light in the waveband of about 623 nm to the infrared region beyond about 700 nm. Both lesion and tissue absorb light in the range of about 525 nm to about 575 nm. This general similarity in the shape of the spectra accounts for the similar appearance of lesion and untreated tissue when viewed with standard video equipment. However, closer inspection of the spectra reveals that lesion spectra exhibit two absorption valleys at about 540 nm and at about 576 nm, and untreated tissue spectra exhibit a single absorption valley at about 555 nm.

Figure 5:
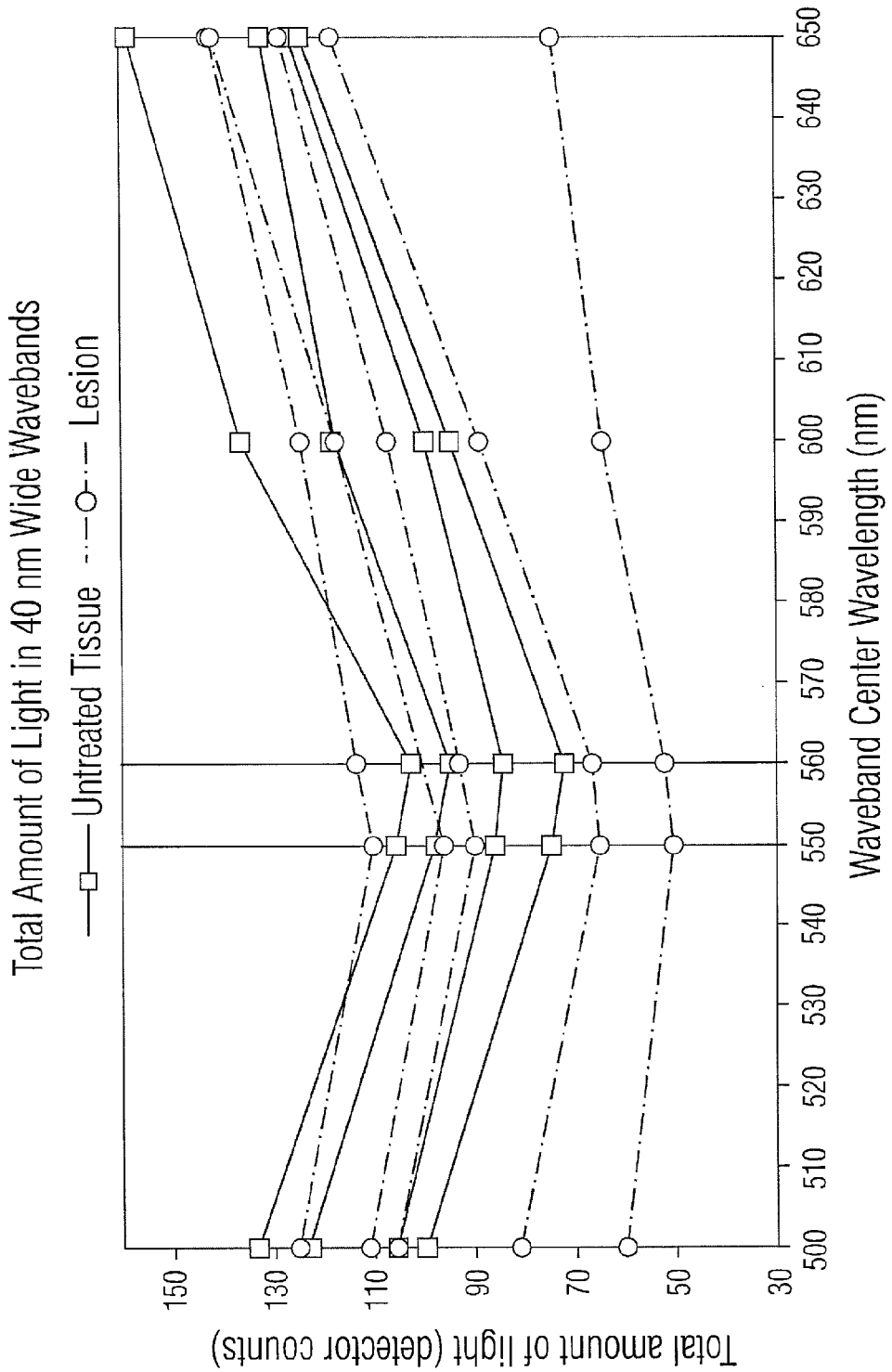
FIG. 5 is a graph showing an amount of light reflected in various 40 nm wavebands centered at 500 nm, 550 nm, 560 nm, 600 nm, and 650 nm.

In utilizing this information, the image module 16 can be configured to analyze spectra data for tissue to determine for any given spectra, how much light there is in any specific waveband. For example, FIG. 5 provides a representation of the relative amount of light in each of four 40 nm wide wavebands centered at 500 nm, 550 nm, 560 nm, and 600 nm for each of the spectra provided in FIG. 4. Forty nm wide wavebands were selected because they are wide enough to collect an adequate amount of light to create an image while still being narrow enough to pick out subtle distinctions between the lesion and de novo tissue spectra. Those skilled in the art will appreciate that filters of various other bandpass widths are within the spirit and scope of the present disclosure. As shown in FIG. 5, for lesions, the amount of light in the waveband centered at about 550 nm is less than the waveband centered at about 560 nm. Conversely, for all the untreated (de novo) tissue spectra, the amount of light in the waveband centered at about 550 nm is greater that that in the waveband centered at about 560 nm.

Based on this experimental data, the chips 54, 56 and corresponding bandpass filters 60, 62 can be configured to distinguish lesions from de novo tissue. That is, the system can include a first chip 54 in communication with a first bandpass filter 60 which is a 40 nm wide filter centered at about 550 nm, and a second chip 56 in communication with a second bandpass filter 62 which is a 40 nm wide filter centered at about 560 nm. The system can also include a third chip 59 in communication with a third filter 64 wherein the third filter 64 can be some other desired waveband, e.g., either in the blue band or in the red band. This third filter 64 provides a third color channel to create an image with more or less natural color, and may not necessarily serve a role in distinguishing lesion from untreated tissue. In use, a red color band is preferred as a third bandpass filter 64 as such a filter would allow facilitate viewing blood.

Referring again to FIGS. 1 and 3, the system 10 can also include a processor 18 in communication with the imaging module 16. More specifically, the processor 18 can be configured to combine images from each of the individual video chips 54, 56, 58 into a single, more or less natural color combined image. The processor 18 can also be configured to determine whether a target tissue is a lesion or untreated tissue by comparing the light absorbed/reflected by the tissue at a first, predetermined waveband as compared to light absorbed/reflected by the tissue at a second, predetermined waveband.

In an exemplary embodiment, the processor 18 can be configured to compare an amount of light reflected within the 550 nm waveband (as imaged by the first chip 54) to the amount of light reflected within the 560 nm waveband for each pixel of the combined image. If the 560 nm band exceeds the 550 nm band, the software can indentify the pixel as a lesion, and the software can apply some false coloring to the pixel. That is, the software can alter the data for this pixel in some manner so that in the combined image, displayed on a video monitor 20 of the system 10, the pixel can be highlighted. Highlighting (i.e., false coloring) can take the form of increasing or decreasing the brightness of pixels identified as lesion or drawing contrasting borders around all pixels identified as lesion. Conversely, if the 550 nm band exceeds the 560 nm band, the software can indentify the pixel as untreated, de novo tissue.

Figure 6:
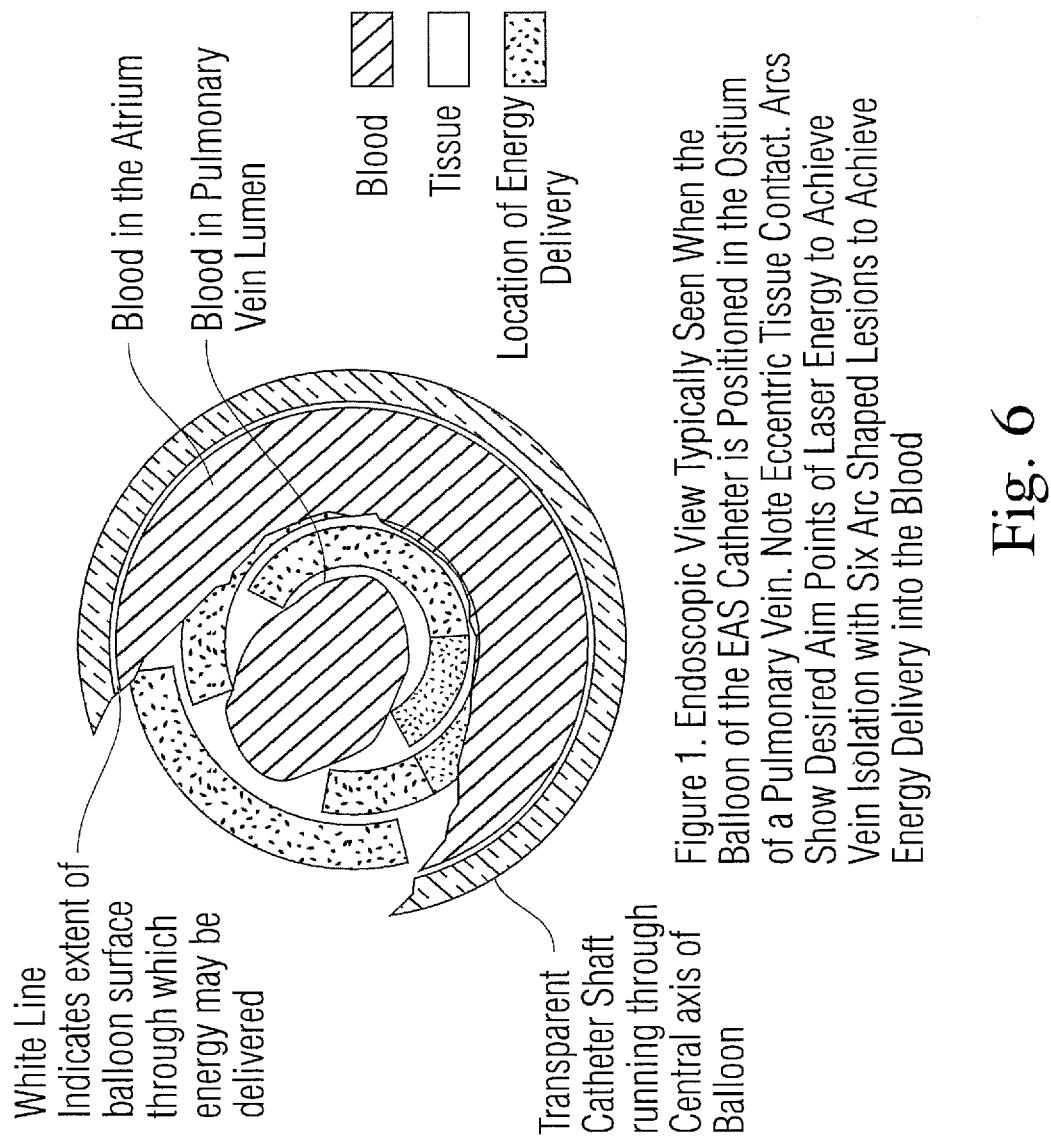
FIG. 6 is a representative view of a treatment site from along a longitudinal axis of a catheter.

FIG. 6 provides an example of a combined image generated by the processor 18 and displayed on a video monitor 20. In use, the video monitor 20 can be configured to receive data from the processor 18 so as to provide a real-time image of the treatment site during ablation. Referring to the example of FIG. 6, the various components/modules of the system provide an image from the perspective of inside an ablation catheter, and looking along a longitudinal axis of catheter, and into a pulmonary vein. As shown, the image provides a user with a clear view of various target areas (e.g., partial ring-like regions extending along portions of the ostium), and also provides false coloring indicative of the treatment status. In this exemplary embodiment, the image indicates 6 partial ring-like target areas with these substantially over-lapping rings providing a circular lesion about the ostium of the pulmonary vein. In use, the clinician can immediately identify and distinguish between those areas which have been treated and those areas in need of ablation.

The above-described visualization and detection systems can be introduced to the treatment site in various manners. For example, in an exemplary embodiment, various components of the system can be incorporated into and/or used in conjunction with a catheter (e.g., a cardiac ablation catheter). In general, the catheter can be any device configured to provide access to the treatment site (e.g., the ostium of the pulmonary vein). Typically, the catheter will have proximal and distal ends with at least one lumen extending therebetween. The lumen(s) can be configured to allow for delivery of various instruments into communication with the target site. For example, a reflectivity sensor, as described above, can be sized and configured so as to be slidably disposed within a lumen of the catheter thereby allowing the sensor to be positioned at any location along the length of the catheter so as to facilitate irradiating the target site. Also, detailed below, an energy emitter can be slidably disposed within the lumen so as to deliver ablation energy to various target regions depending at least in part on the linear position of the ablation element relative to the catheter.

Figure 7:
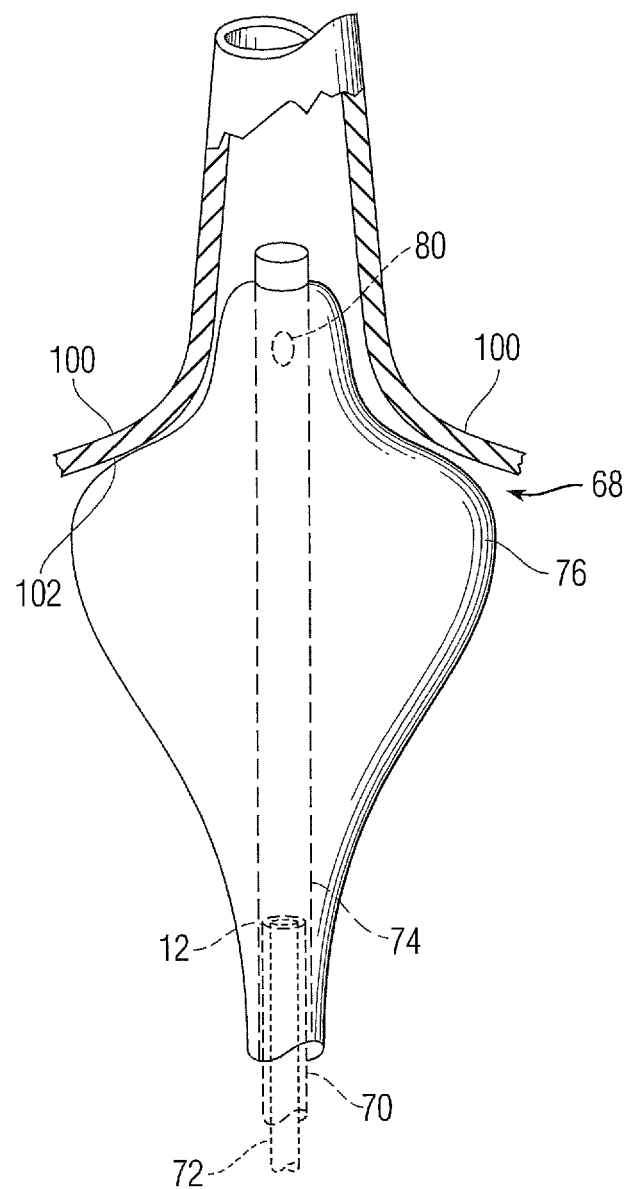
FIG. 7 is a schematic representation of an exemplary embodiment of an ablation catheter positioned adjacent an ostium of a pulmonary vein.

FIG. 7 provides an exemplary embodiment of an ablation catheter instrument 68 positioned adjacent an ostium 100 of a pulmonary vein, and having an ablation/visualization system 72 slidably disposed therein. As shown, the instrument 68 can include an elongate catheter 14 having an inflation balloon 76 coupled to the distal end of the catheter 14, and, upon inflation, the balloon 76 can be configured to provide substantially constant contact points 102 between portions of the balloon 76 and a circumference of the ostium 100 of the pulmonary vein. During an ablation procedure, this continuous circumferential ring provides a target region by removing blood from the area between the balloon and the tissue. As shown in FIG. 6 above, the visualization system 10 can provide a clinician with a real time view of the contact area between the balloon 76 and the ostium 100, as well as the treatment status of the various target sites (e.g., the partial rings shown in FIG. 6).

Additionally, the balloon 76 can have a shape configured to facilitate the desired procedure. For example, as shown in FIG. 7, the balloon 76 can have a tear-drop shape thereby facilitating against over-insertion of the balloon 76 into the pulmonary vein. The balloon 76 can also be formed of various materials (including both compliant and non-compliant materials). Various embodiments of such balloons are detailed in Applicants' co-pending patent applications U.S. Ser. No. 10/357,156, filed Feb. 3, 2003, U.S. Ser. No. 11/504,354, filed Aug. 15, 2006, and U.S. Ser. No. 10/865,558, filed Jun. 10, 2004, the entirety of each of these applications being incorporated herein by reference.

Figures 8A, 8B:
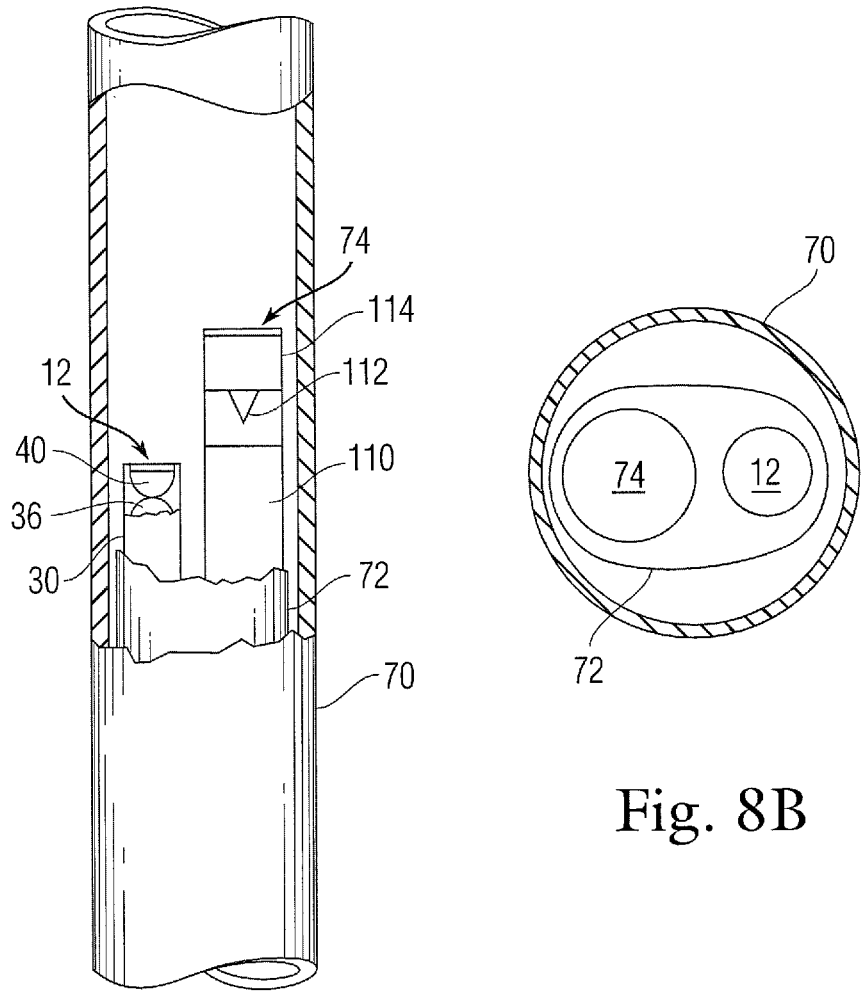
FIG. 8A is a side view of an embodiment of an ablation catheter showing a reflectivity sensor and an energy emitter disposed therein.
FIG. 8B is a top view of the embodiment of FIG. 8A.

FIGS. 8A and 8B also provide an example of a cardiac ablation catheter 70 which includes both a reflectivity sensor 14 and an energy emitter 70 (i.e., an ablation/visualization system 72) disposed therein. As shown, the reflectivity sensor 14 resides in a first lumen, and the energy emitter 70 resides in a second lumen extending substantially parallel to the first lumen. In some embodiments, not shown, the illumination source can be disposed in yet another lumen of the catheter. Each the reflectivity sensor 14 and the energy emitter 70 can be slidably disposed within their respective lumens thereby allowing each component 14, 70 to be independently positioned at any location along the length of the catheter 70. In certain ablation procedures, such as the treatment of atrial fibrillation, the ability to independently position these elements facilitates treatment by allowing numerous regions to be treated and/or visualized without moving the catheter 70.

Various embodiments of the energy emitter 74 can be incorporated into the cardiac ablation catheter 68. In general, the energy emitter 74 can be any element capable of delivering an amount, power, configuration, and/or shape (e.g., partial ring, complete ring, spot) of ablation energy to a target area. For example, as shown in FIG. 8A, the radiant energy emitter 74 can include at least one optical fiber 110 in communication with an optical element(s) 112, 114, which cooperate to deliver ablative light energy through the instrument 68 to the target site. The catheter body 14, projection balloon 76, and inflation/ablation fluids (if present) are all preferably substantially transparent to the radiant energy at the selected wavelength to provide a low-loss transmission pathway from the ablation element 74 to the target.

Various embodiments of the energy emitter 74 are disclosed in Applicants' co-pending patent applications U.S. Ser. No. 10/357,156, filed Feb. 3, 2003, U.S. Ser. No. 11/504,354, filed Aug. 15, 2006, and U.S. Ser. No. 10/865,558, filed Jun. 10, 2004, the entirety of each of these applications being incorporated herein by reference.

FIGS. 9A and 9B illustrate an advantage of an independently positionable energy emitter 74 which is slidably disposed within a lumen of the catheter 70. Because the radiant energy emitter does not require contact with a target tissue region and is, in fact, decoupled from the rest of the instrument 68, the clinician is free to select a desired target region by simply moving the emitter 74 within and relative to the lumen of the catheter 70. As shown in FIG. 9A, the radiant energy emitter 74 can be positioned to form a ring-like lesion at a particular location by positioning the radiant energy emitter 74 at the rear of the projection balloon 76—at a distance from the target tissue denoted as "C". Alternatively, a smaller ring-like lesion can be formed by positioning the radiant energy emitter 74 closer to the front of the projection balloon 76, as shown in positions "A" or "B". Smaller lesions can be preferably when the geometer of the vein ostium presents a sharper change in diameter. Also, it may be desirable to change the intensity of the emitted radiation depending upon the distance it must be projected. For example, a more intense radiant energy beam may be desirable in the scheme illustrated in position "C" in comparison with position "A".

Moreover, in some instances the geometries of the pulmonary vein (or the orientation of the projection balloon relative to the ostium) may be such that no single annular lesion can form a continuous conduction block. Again, the present invention provides a mechanism for addressing this problem by adjustment of the location of the energy emitter to form two or more partially circumferential lesions. As shown in FIG. 9B, the devices of the present invention can form a first lesion 130 and a second lesion 132, each in the form of an arc or partial ring. Because each lesion has a thickness (dependent largely by the amount of energy deposited into the tissue) the two lesions can axially combine, as shown, to form a continuous encircling or circumscribing lesion that blocks conduction.

Referring back to FIG. 6, some ablation procedures require an energy emitter 74 configured to deliver partial rings and/or "spots" of ablative energy to any of a plurality of target regions. That is, in the case of treating atrial fibrillation, the energy emitter 74 can be configured to slide and rotate relative to the substantially stationary catheter 14 so as to deliver a plurality of partial ring-like or spot lesions to corresponding locations. This treatment can continue until each of the plurality of treatment regions has been targeted (i.e., ablated) thereby providing a continuous circumferential lesion surrounding the pulmonary vein which is essentially formed of a plurality of overlapping lesions.

Figure 10:
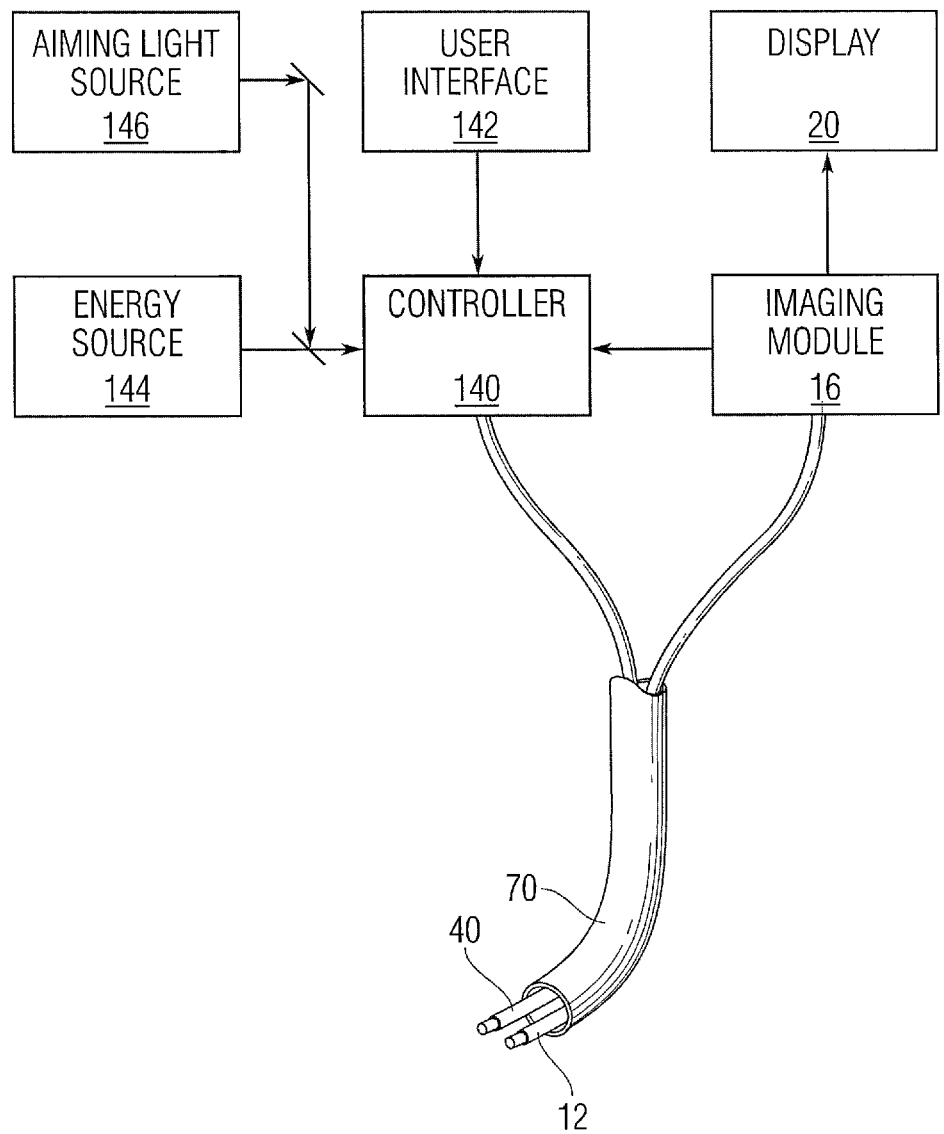
FIG. 10 is a representation of an embodiment of a visualization system incorporated into a cardiac ablation system.

FIG. 10 is a schematic block diagram illustrating the visualization/ablation instrument 68 comprising a reflectivity sensor 12 and ablation element 74 connected to an analyzer system. The analyzer system can include the imaging module 16, discussed above, which can further be in communication with a display module 20 (via a processor, detailed above) for clinician viewing. The display 20 can be a monitor or a heads-up projection onto glasses worn by members of the surgical team.

The system can further include an energy source 144, a controller 144, and/or a user interface 142. In use, the illumination source (shown in FIG. 1) directs light to the target site and the reflectivity sensor 12 detects and transfers image data to/from the treatment to the image module 16 for processing by the imaging module 16 and/or controller 140 to determine whether a suitable ablation path can be created. In one embodiment, the system can further include an aiming light source 146 which can also be used to visualize the location where energy will be delivered to the tissue. If a suitable ablation path is seen by the surgeon, the controller 140 can transmit radiant energy from the ablation element 74 to a target tissue site to effect ablation. The controller 140 can further provide simulated displays to the user, superimposing, for example, a predicted lesion pattern on the image acquired by the imaging module 16 or superimposing dosimetry information based on the lesion location. The controller 140 can further include a memory for storing and displaying data, such as pre-procedure images, lesion predictions and/or actual outcomes. The controller 140 can further provide a safety shutoff to the system in the event that a clear transmission pathway between the radiant energy source and the target tissue is lost during energy delivery.

Additionally, various embodiments of methods for distinguishing lesions from de novo tissue during various ablation procedures are provided herein. In an exemplary embodiment, a method for treating atrial fibrillation is provided which includes selecting and/or identifying a plurality of partial ring-like tissue areas surrounding an ostium of a pulmonary vein. These ring-like tissue areas are selected such that, when taken together, the tissue areas form a substantially continuous lesion around the ostium. Thus, the tissue areas are typically over-lapping partial rings of tissue.

In use, the visualization system allows a user to accurately identify the starting point and end point of a partial ring-like tissue lesion. Thus, the user can begin a second lesion at the end point of a first lesion thereby providing a continuous circumferential lesion made up of a plurality of accurately and efficiently delivered partial lesions.

The methods can utilize various embodiments of the above-described visualization system to determine which if a particular area is already a lesion (i.e., from a prior treatment) or if the area is de novo tissue in need of treatment. That is, the method can include irradiating the area with light from a reflective sensor which is disposed within a cardiac catheter, and analyzing the reflectivity/absorbance data resulting from the irradiation by a imaging module. As detailed above, the imaging module can detect reflectivity data at at least two pre-determined wavebands (e.g., centered at about 550 nm and 560 nm, respectively) wherein a processor can compare this information to determine if the tissue is a lesion or de novo tissue. The clinician can then utilize this information (by viewing a real-time video monitor) to ablate de novo tissue and/or to prevent over-treatment of a lesion.

Although described in connection with cardiac ablation procedures, it should be clear that the instruments of the present invention can be used for a variety of other procedures where treatment with radiant energy is desirable, including laparoscopic, endoluminal, perivisceral, endoscopic, thoracoscopic, intra-articular and hybrid approaches.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A tissue visualization system, comprising:
a reflectivity sensor sized and shaped to be slidably disposed within a lumen of a catheter, and configured to capture reflected light from an area of tissue;
an imaging module in communication with the reflectivity sensor, and configured to detect a first amount of light reflected by the area of tissue at a first, predetermined waveband and a second amount of light reflected by the area of tissue at a second, predetermined waveband;
a processor in communication with the imaging module, and configured in real time to compare the first amount of light relative to the second amount of light, and further configured in real time to classify the area of tissue as a lesion or as de novo tissue if the first amount of light is less than or greater than the second amount of light, respectively; and a display that is in communication with the processor for displaying, in real time, an image of the area of tissue obtained from the imaging module, wherein the processor is configured to visually differentiate, on the display, tissue that is classified as a lesion from de novo tissue to allow a user to distinguish the lesion from de novo tissue on the display and evaluate a progress of a medical procedure;

wherein the first and second wavebands are specifically selected such that a comparison between a degree of light reflectance at each of the first and second wavebands is indicative of whether the tissue being analyzed is a lesion or de novo tissue.

2. The system of claim 1, wherein the first, predetermined waveband is centered at 550 nm, and the second, predetermined waveband is centered at 560 nm.

3. The system of claim 2, wherein each waveband is 40 nm wide.

4. The system of claim 1, wherein the imaging module includes a video camera having a plurality of video chips with at least a first and a second video chip configured to generate a first image and a second image based on the first predetermined wavelength band and the second predetermined wavelength band, respectively.

5. The system of claim 4, wherein the first predetermined wavelength band is centered at 550 nm, and the second wavelength band is centered at 560 nm.

6. The system of claim 5, wherein the first and the second video chips are in communication with a first and a second 40 nm wide bandpass filter, respectively.

7. The system of claim 4, wherein the video camera further includes a third video chip configured to generate a third image based on a third predetermined wavelength band which is selected from a red waveband or a blue waveband.

8. The system of claim 4, wherein the processor is configured to generate a combined image from the first image and the second image generated by the first and second video chips, respectively, the combined image being the image that is displayed on the display.

9. The system of claim 8, wherein the visual differentiation performed by the processor on the image comprises a false coloring indicative of a treatment status that is applied to at least a portion of the combined image.

10. The system of claim 9, wherein the processor is configured to apply a false coloring to any portion of the combined image which is classified as lesion.

11. The system of claim 9, wherein the display comprises a video monitor configured to display a real-time view of the combined image.

12. The system of claim 1, wherein the reflectivity sensor is a fiber-optic endoscope.

13. The system of claim 12, further including a fiber optic energy emitter configured to irradiate partial ring-like areas of tissue.

* * * * *